US005692603A

United States Patent [19]
Stotesbury

[11] Patent Number: 5,692,603
[45] Date of Patent: Dec. 2, 1997

[54] TOOTHBRUSH CASE

[76] Inventor: Dean L. Stotesbury, 507 S. Guadalupe Ave., Redondo Beach, Calif. 90277

[21] Appl. No.: 410,329

[22] Filed: Mar. 24, 1995

[51] Int. Cl.$^6$ ............................................. B65D 85/20
[52] U.S. Cl. ............................. 206/209.1; 206/362.2
[58] Field of Search ........................ 206/362.2, 362.1, 206/362.3, 361, 209.1, 581; 132/308, 309, 310, 311

[56] References Cited

U.S. PATENT DOCUMENTS

| | | |
|---|---|---|
| 615,357 | 12/1898 | Johnson et al. . |
| 1,051,433 | 1/1913 | Moseley et al. . |
| 1,451,425 | 4/1923 | Hurley ........................ 206/209.1 |
| 1,586,332 | 5/1926 | Scott ........................... 206/209.1 |
| 1,833,205 | 11/1931 | Case ................................ 132/310 |
| 2,508,773 | 5/1950 | Reichmuth ................... 206/209.1 |
| 3,741,378 | 6/1973 | Parker ............................ 206/361 |
| 4,115,082 | 9/1978 | Newell .............................. 55/103 |
| 4,214,657 | 7/1980 | Winston ....................... 206/209.1 |
| 4,806,770 | 2/1989 | Hylton et al. ................. 250/455.1 |
| 4,884,688 | 12/1989 | Hurst ............................ 206/362.2 |
| 4,902,306 | 2/1990 | Burnett et al. .................... 55/6 |
| 4,997,629 | 3/1991 | Morchand et al. ........... 206/362.1 X |
| 5,037,455 | 8/1991 | Scheineson et al. ............. 55/103 |
| 5,076,428 | 12/1991 | Shaw ............................ 206/362.2 |
| 5,126,572 | 6/1992 | Chu .............................. 250/455.1 |
| 5,188,646 | 2/1993 | Nolen, Jr. ......................... 55/155 |
| 5,375,711 | 12/1994 | Bree et al. .................... 206/362.2 |

FOREIGN PATENT DOCUMENTS 256706  8/1947  Switzerland .

Primary Examiner—Jacob K. Ackun
Attorney, Agent, or Firm—William R. Sharp

[57]  ABSTRACT

A toothbrush case comprises mateable case members and an associated pair of filters. Such filters, preferably of the electrostatic type, remove contaminants from air flowing into the case, and therefore allow flow of substantially contaminant-free air through the case between the filters and around a toothbrush as stored within the case. This assists in evaporation of moisture that is present on the toothbrush (particularly the bristles) or on interior surfaces of the case. Contamination of the toothbrush and the bristles thereof is consequently minimized.

10 Claims, 1 Drawing Sheet

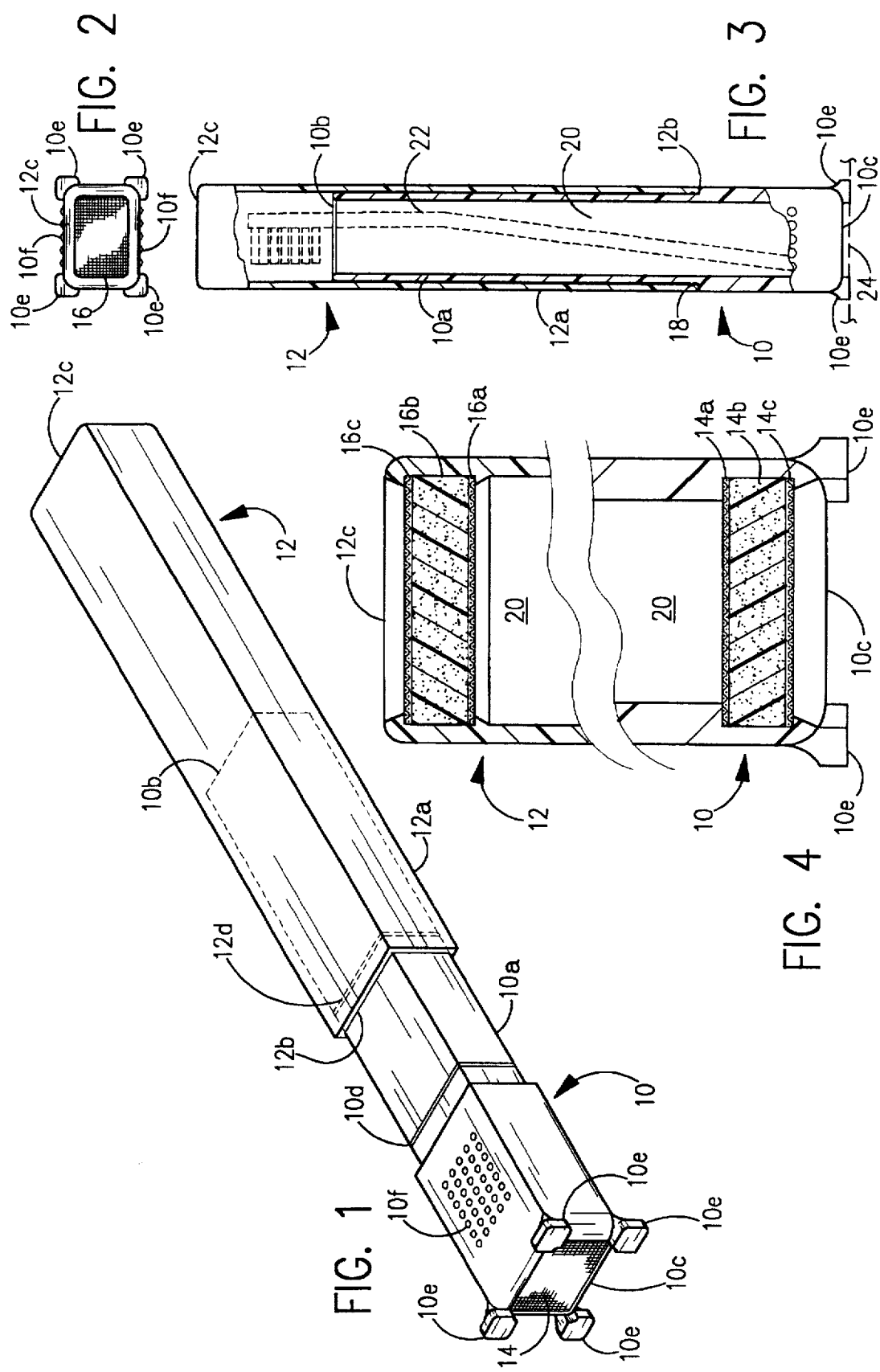

TOOTHBRUSH CASE

BACKGROUND OF THE INVENTION

This invention relates to a toothbrush case which provides a hygienic environment therein for storage of a toothbrush when not in use.

A toothbrush is typically kept in a highly contaminated environment such as a bathroom, or possibly in a suitcase while traveling. An exposed toothbrush in a bathroom environment, in particular, is contaminated by a number of sources, such as a nearby flushing toilet, the blow drying of hair, inadvertent contact with other toothbrushes, and coughing and sneezing of persons in the bathroom.

SUMMARY OF THE INVENTION

It is, therefore, an object of the invention to provide a toothbrush case which provides a hygienic environment therein so as to minimize contamination of the bristles of a toothbrush within the case.

It is also an object of the invention that such toothbrush case is simple and inexpensive in construction.

It is yet another object of the invention that such toothbrush case is highly portable for optimum convenience.

The above objects are realized in a toothbrush case comprising: a first case member; a second case member mateable with the first case member so as to define a chamber therein in which a toothbrush can be positioned; a first filter means through which the chamber is in communication with the environment exterior to the case so as to allow flow of air between the exterior environment and the chamber through the first filter means, wherein the first filter means removes contaminants from air which flows from the exterior environment and through the first filter means into the chamber; and a second filter means through which the chamber is in communication with the exterior environment so as to allow flow of air between such exterior environment and the chamber through the second filter means, wherein the second filter means removes contaminants from air which flows from the exterior environment and through the second filter means into the chamber, and wherein the second filter means is spaced from and positioned relative to the first filter means to allow flow of substantially contaminant-free air through the chamber, between the first and second filter means, and around a toothbrush as positioned in the chamber.

According to a preferred embodiment of the invention described hereafter, each of the filters is an electrostatic filter most preferably comprised of two layers of polypropylene fibers and an intermediate polyurethane layer. Each case member has a corresponding filter at one end thereof. Mating and separation of the case members by means of male and female mating portions causes a flow of air through the filters which acts to develop the desired charges in the filter layers.

The toothbrush case of the invention, therefore, isolates a toothbrush from the contaminated exterior environment by not only enclosing the toothbrush therein, but also by employing the filters to allow circulation of substantially contaminant-free air through the case. Such circulation of substantially contaminant-free air assists in evaporating moisture that is present on the toothbrush or on the interior surfaces of the case. Potentially harmful contaminants such as bacteria and other microbes thrive in a moist environment, and generally die when such moisture evaporates. Furthermore, the toothbrush case is simple and inexpensive in construction, insofar as it requires only the case members and associated filters as components of the case, and is also highly portable to allow ease of use in traveling and in transport to the workplace or other site away from home.

BRIEF DESCRIPTION OF THE DRAWINGS

FIG. 1 is a perspective view of the partially mated case members of a toothbrush case in accordance with the invention.

FIG. 2 is a view of one end of a case member which is not visible in FIG. 1.

FIG. 3 is a partial and longitudinal cross-sectional view of the toothbrush case of FIG. 1 with its case members in their fully mated positions.

FIG. 4 is an enlarged, cross-sectional view of only end portions of the toothbrush case clearly showing the structure of filters associated with such end portions.

DETAILED DESCRIPTION OF THE INVENTION

A preferred embodiment of the invention will now be described with reference to the FIGURES.

Referring to FIGS. 1 and 2, the illustrated toothbrush case comprises: a tubular case member 10 having a male mating portion 10a and opposing open ends 10b and 10c; a tubular case member 12 having a female mating portion 12a and opposing open ends 12b and 12c; a filter 14, of which only one surface is visible in FIG. 1, fixedly mounted near or at open end 10c; and a filter 16, of which only one surface is visible in FIG. 2, fixedly mounted near or at open end 12c. As shown, male mating portion 10a is shaped and sized to be received within female mating portion 12a, and is provided with a generally annular rib 10d adapted to sealingly engage a generally annular internal groove 12d (shown as a broken line) in female portion 12a when case members 10 and 12 are fully mated. Case member 10 also preferably has four feet 10e projecting from the corners of end 10c, and knobs 10f on the exterior surface to assist the user in grasping case member 10 with his or her fingers.

As shown, male mating portion 10a is preferably a substantial portion, lengthwise, of case member 10. Similarly, female mating portion 12a is a substantial portion, lengthwise, of case member 12. This feature is important in charging of the filters as will be apparent in subsequent discussion.

Case members 10 and 12 can be any suitably moldable material which is substantially rigid. A plastic material is preferred, and a substantially transparent acrylic resin is particularly preferred. Substantially transparent case members permits the user to see a toothbrush as stored therein, thus enabling the user to identify his or her toothbrush in the case among a number of cases containing toothbrushes of other family members.

Referring now to FIG. 3, this partial cross-sectional view of the toothbrush case of FIG. 1 shows case members 10 and 12 in their fully mated positions, wherein male mating portion 10a is fully received within female mating portion 12a so as to sealingly engage such female mating portion near open end 12b at rib and groove joint 18. It should be apparent that female mating portion 12a, although substantially rigid, is sufficiently flexible to permit snapping of rib 10d into groove 12d to thereby form joint 18. Therefore, open ends 10c and 12c define opposing ends of the toothbrush case, whereas open ends 10b and 12b are intermediate the thus defined opposing ends of the toothbrush case. The mated case members accordingly define a chamber 20 in which a toothbrush 22, having bristles and shown in broken lines, can be positioned when not in use.

The toothbrush case can be positioned substantially vertically by resting upon feet 10e as shown. Feet 10e can accordingly be in contact with a suitable horizontal surface, as indicated by the broken line at 24, in a manner to thereby separate open end 10c from surface 24 to allow air flow through open end 10c. The handle end of toothbrush 22 can merely rest upon filter 14 when the case is positioned vertically. It should be understood, however, that the toothbrush case can also be positioned horizontally without adversely affecting its performance.

Referring now to FIG. 4, this enlarged cross-sectional view shows filter 14 as comprising layers 14a, 14b, and 14c and as being fixedly mounted near open end 10c within a corresponding generally annular slot defined within case member 10. Layer 14b as the intermediate layer is positioned between layers 14a and 14c. Similarly, filter 16 comprises layers 16a, 16b, and 16c and is fixedly mounted near open end 12c within a corresponding generally annular slot defined within case member 12. Layer 16b as the intermediate layer is positioned between layers 16a and 16c.

Chamber 20 is in communication with the environment exterior to the toothbrush case through filters 14 and 16 so as to allow air flow between chamber 20 and the exterior environment through the filters, and in particular through the layers of each filter in sequence. Each of filters 14 and 16 functions to remove contaminants from air which flows from the exterior environment and through such filter into chamber 20. The term "contaminants" as used herein and in the appended claims is broadly defined to include any particles present in air other than the constituent gases of air. Such contaminants can include, for example, bacteria and virus-containing particles as well as mold spores, mildew particles, pollen, etc. Filters 14 and 16, as longitudinally spaced from one another and near opposing ends of the toothbrush case, allow flow of substantially contaminant-free air through chamber 20, between the filters, and around a toothbrush (particularly the bristles) in chamber 20 to assist in evaporation of any moisture that is present on the toothbrush or on the surfaces that define the chamber. This is advantageous for reasons discussed previously.

Filters 14 and 16 in the illustrated embodiment are electrostatic filters of which each component layer is preferably a porous organopolymeric material capable of developing and holding an electrostatic charge. Each of layers 14a, 14c, 16a, and 16c is most preferably a mesh of polypropylene fibers capable of developing and holding a negative electrostatic charge upon flow of air therethrough. Each of layers 14b and 16b is most preferably an open cell foam polyurethane capable of developing and holding a positive electrostatic charge upon flow of air therethrough. Charging of the various filter layers is assisted by air flow through the filter layers upon mating and unmating of case members 10 and 12. In this regard, it is desirable for the user to pick up case member 10 as well as case member 12 and move each of such case members together or apart in the mating or unmating operation. Natural convection currents and consequent circulation of air through the case when stationary also assists in charging of the filter layers.

The various filter layers of filters 14 and 16 can optionally be treated with a suitable antibacterial/antimicrobe agent in order to further reduce contamination. The AEGIS® antibacterial/antimicrobe treatment is suitable for this purpose.

Finally, filters 14 and 16 can be periodically cleaned by simply running warm tap water through them. This will not adversely affect their performance.

Obviously, many modifications and variations of the present invention are possible in light of the above teachings. It is, therefore, to be understood that within the scope of the appended claims, the invention may be practiced otherwise than as specifically described.

That which is claimed is:

1. A toothbrush case comprising:

a first case member;

a second case member mateable with the first case member so as to define a chamber therein in which a toothbrush can be positioned;

an electrostatic first filter means through which the chamber is in communication with the environment exterior to the case so as to allow flow of air between the exterior environment and the chamber through the first filter means, wherein the first filter means removes contaminants from air which flows from the exterior environment and through the first filter means into the chamber; and an electrostatic second filter means through which the chamber is in communication with the exterior environment so as to allow flow of air between such exterior environment and the chamber through the second filter means, wherein the second filter means removes contaminants from air which flows from the exterior environment and through the second filter means into the chamber, and wherein the second filter means is spaced from and positioned relative to the first filter means to allow flow of substantially contaminant-free air through the chamber, between the first and second filter means, and around a toothbrush as positioned in the chamber.

2. A toothbrush case as recited in claim 1 wherein each filter means comprises a plurality of layers, each layer comprising a porous organopolymeric material capable of developing and holding an electrostatic charge.

3. A toothbrush case as recited in claim 2 wherein each filter means comprises: a first layer comprising a mesh of polypropylene fibers; a second layer comprising a mesh of polypropylene fibers; and a third layer comprising open cell foam polyurethane positioned between the first and second layers; wherein the layers are oriented to receive air flow through such layers in sequence.

4. A toothbrush case as recited in claim 3 wherein the first case member has a first mating portion and the second case member has a second mating portion, and wherein the first mating portion sealingly engages the second mating portion when the case members are fully mated.

5. A toothbrush case as recited in claim 4 wherein the first mating portion has a generally annular rib and the second mating portion has a generally annular groove, the generally annular rib being adapted to sealingly engage the generally annular groove.

6. A toothbrush case as recited in claim 5 wherein the first mating portion is a substantial portion of the first case member and the second mating portion is a substantial portion of the second case member.

7. A toothbrush case as recited in claim 6 wherein the first mating portion is a male mating portion which is shaped and sized to be received within the second mating portion as a female mating portion.

8. A toothbrush case as recited in claim 7 wherein the first case member is a tubular member having opposing open ends and having the first filter means fixedly mounted therein near or at one open end thereof, and wherein the second case member is a tubular member having opposing open ends and having the second filter means fixedly mounted therein near or at one open end thereof, and further wherein said one open end of the first case member and said one open end of the second case member respectively define opposing ends of the toothbrush case having both case members fully mated, and the other open ends are intermediate the thus defined opposing ends of the toothbrush case.

9. A toothbrush case as recited in claim 8 further comprising a plurality of feet associated with one end of the toothbrush case upon which the toothbrush case can rest in a substantially vertical position upon a surface.

10. A toothbrush case as recited in claim 9 wherein each case member is comprised of a substantially rigid plastic.

* * * * *